United States Patent [19]

Silva

[11] Patent Number: 4,616,077

[45] Date of Patent: Oct. 7, 1986

[54] METHOD FOR PREPARING CYCLIC POLYCARBONATE OLIGOMER FROM BISCHLOROFORMATE COMPOSITION

[75] Inventor: James M. Silva, Clifton Park, N.Y.

[73] Assignee: General Electric Company, Schenectady, N.Y.

[21] Appl. No.: 800,865

[22] Filed: Nov. 22, 1985

[51] Int. Cl.[4] ............................................ C08G 63/62
[52] U.S. Cl. .................................... 528/371; 528/86; 528/370; 528/372
[58] Field of Search ............... 528/371, 370, 372, 198, 528/196, 199, 86

[56] References Cited

U.S. PATENT DOCUMENTS 3,269,985  8/1966  Loncrini ............................. 528/371
3,274,214  9/1966  Prochaska ........................... 528/371
3,312,660  4/1967  Kurkly et al. ....................... 528/371
3,386,954  6/1968  Schnell et al. ...................... 528/370

Primary Examiner—Harold D. Anderson
Attorney, Agent, or Firm—William H. Pittman; James C. Davis, Jr.; James Magee, Jr.

[57] ABSTRACT

Cyclic polycarbonate oligomers are prepared by a method which is adaptable to continuous operation, by the reaction of a bisphenol bischloroformate (e.g., bisphenol A bischloroformate) with an amine (e.g., triethylamine) and an alkali metal hydroxide in a tank reactor (preferably a continuous stirred tank reactor) in a mixed aqueous-organic system, with agitation (preferably by stirring) at a rate just sufficient to prevent segregation of the aqueous and organic liquid phases. The residence time of the mixture in the reactor is preferably about 8–12 minutes.

16 Claims, No Drawings

METHOD FOR PREPARING CYCLIC POLYCARBONATE OLIGOMER FROM BISCHLOROFORMATE COMPOSITION

This invention relates to cyclic polycarbonate oligomers and methods for their preparation. More particularly, it relates to an improved method which is readily adaptable to continuous operation.

Cyclic aromatic polycarbonate oligomers convertible to linear polycarbonates, often of very high molecular weight, are known. Such oligomers may be pure compounds such as the trimer or tetramer, as disclosed, for example, in the following U.S. patents:
U.S. Pat. No. 3,155,683
U.S. Pat. No. 3,386,954
U.S. Pat. No. 3,274,214
U.S. Pat. No. 3,422,119.

For many purposes, cyclic polycarbonate oligomer mixtures are preferred since they can be more easily handled and polymerized. The preparation of oligomer mixtures of this type is disclosed in copending, commonly owned application Ser. No. 704,122, filed Feb. 22, 1985, the disclosure of which is incorporated by reference herein. Preparation is typically by the reaction of a corresponding bischloroformate composition with an alkali metal hydroxide and a tertiary amine.

In view of the utilities of cyclic polycarbonate oligomers, there is continued interest in inexpensive, efficient methods for their preparation. In particular, a method adaptable to continuous operation would be advantageous.

A problem in the preparation of cyclic polycarbonate oligomers is the simultaneous production of linear polycarbonates (hereinafter sometimes denoted "linears") as by-products. It is frequently necessary to remove the linears before using the cyclic oligomers. If large proportions of linears are obtained, the yield of cyclics decreases and the cost of producing the cyclics increases correspondingly.

A principal object of the present invention, therefore, is to provide a relatively simple, inexpensive method for preparing cyclic polycarbonate oligomers.

A further object is to provide a method which requires only a short time and can be easily conducted in readily available equipment.

A further object is to provide a method which can be adapted to minimize the production of linears.

A still further object is to provide a method which is readily adaptable to continuous operation.

Other objects will in part be obvious and will in part appear hereinafter.

In its broadest definition, the present invention is a method for preparing a composition comprising cyclic polycarbonate oligomers characterized by structural units of the formula

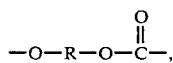

wherein R is a divalent aromatic radical, which comprises:
simultaneously charging the following reagents to a tank reactor:
(A) a bischloroformate composition consisting essentially of bischloroformates of the formula

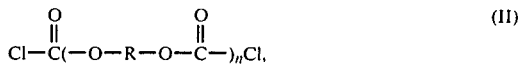

wherein n is at most 4 in a major proportion of said bischloroformates;
(B) at least one aliphatic or heterocyclic tertiary amine which dissolves preferentially in the organic phase of the reaction mixture;
(C) an aqueous alkali metal hydroxide solution; and
(D) a substantially non-polar organic liquid which forms a two-phase system with water;
reagent A being charged separately from reagents B and C:
while maintaining the reaction mixture in said tank reactor under agitation conditions just sufficient to prevent segregation of the aqueous and organic liquid phases;
allowing said reagents to react for a period of time sufficient to form the desired cyclic oligomers; and
recovering said oligomers.

The R values in the bischloroformate compositions and cyclic polycarbonate oligomer products involved in the present invention are divalent aromatic radicals such as m-phenylene, p-phenylene, 4,4'-bisphenylene and 2,2-bis(4-phenylene)propane. Other suitable radicals are those which correspond to the dihydroxy compounds disclosed by name or formula (generic or specific) in U.S. Pat. No. 4,217,438, the disclosure of which is incorporated by reference herein. Also included are radicals containing non-hydrocarbon moieties. These may be substituents such as chloro, nitro, alkoxy and the like, and also linking radicals such as thio, sulfoxy, sulfone, ester, amide, ether and carbonyl. Most often, however, all R radicals are hydrocarbon radicals.

The R radicals preferably have the formula

wherein each of $A^1$ and $A^2$ is a single-ring divalent aromatic radical and Y is a bridging radical in which one or two atoms separate $A^1$ from $A^2$. The free valence bonds in formula III are usually in the meta or para-positions of $A_1$ and $A^2$ in relation to Y. Such R values may be considered as being derived from bisphenols of the formula HO—$A^1$—Y—$A^2$—OH. Frequent reference to bisphenols will be made hereinafter, but it should be understood that R values derived from suitable compounds other than bisphenols may be employed as appropriate.

In formula III, the $A^1$ and $A^2$ values may be unsubstituted phenylene radicals or substituted derivatives thereof, illustrative substituents (one or more) being alkyl, alkenyl (e.g., crosslinkable-graftable moieties such as vinyl and allyl), halo (especially chloro and/or bromo), nitro, alkoxy and the like. Unsubstituted phenylene radicals are preferred. Both $A^1$ and $A^2$ are preferably p-phenylene, although both may be o- or m-phenylene or one o- or m-phenylene and the other p-phenylene.

The bridging radical, Y, is one in which one or two atoms, preferably one, separate $A^1$ from $A^2$. It is most often a hydrocarbon radical and particularly a saturated radical such as methylene, cyclohexylmethylene, 2-[2.2.1]-bicycloheptylmethylene, ethylene, isopropylidene, neopentylidene, cyclohexylidene, cyclopentadecylidene, cyclododecylidene or adamantylidene, especially a gem-alkylene radical. Also included, however, are unsaturated radicals and radicals which are entirely or partially composed of atoms other than carbon and hydrogen. Examples of such radicals are 2,2-dichloroethylidene, carbonyl, thio and sulfone. For reasons of availability and particular suitability for the purposes of this invention, the preferred radical of formula III is the 2,2-bis(4-phenylene)propane radical, which is derived from bisphenol A and in which Y is isopropylidene and $A^1$ and $A^2$ are each p-phenylene.

Reagent A in the method of this invention is a bischloroformate composition which may be monomeric bisphenol bischloroformate employed in substantially pure, isolated form, but is more often a crude bischloroformate product. Suitable crude products may be prepared by any known methods for bischloroformate preparation. Typically, at least one bisphenol is reacted with phosgene in the presence of a substantially inert organic liquid, as disclosed in the following U.S. patents:

U.S. Pat. No. 3,255,230
U.S. Pat. No. 3,966,785
U.S. Pat. No. 3,312,661
U.S. Pat. No. 3,974,126

The disclosures of these patents are incorporated by reference herein. In addition to monomer bischloroformate, such crude bischloroformate product may contain oligomer bischloroformates; preferably, a major proportion of said product consists of bischloroformates containing up to 4 structural (i.e., bisphenol) units. It may also contain minor amounts of higher oligomer bischloroformates and of monochloroformates corresponding to any of the aforementioned bischloroformates.

The preparation of the crude bischloroformate product preferably takes place in the presence of aqueous alkali. The pH of the reaction mixture may be up to about 14 and is preferably no higher than about 12. It is generally found, however, that the proportion of linears in the cyclic oligomer mixture is minimized by employing a crude bischloroformate product comprising a major amount of bisphenol bischloroformate and only minor amounts of any oligomer bischloroformates. Such products may be obtained by the method disclosed in copending, commonly owned application Ser. No. 790,909, filed Oct. 24, 1985, the disclosure of which is also incorporated by reference herein. In that method, phosgene is passed into a mixture of a substantially inert organic liquid and a bisphenol, said mixture being maintained at a temperature within the range of about 10°–40° C., the phosgene flow rate being at least 0.15 equivalent per equivalent of bisphenol per minute when the temperature is above 30° C. An aqueous alkali metal or alkaline earth metal base solution is simultaneously introduced as necessary to maintain the pH in the range of 0–8. By this method, it is possible to prepare bischloroformate in high yield while using a relatively small proportion of phosgene, typically up to about 1.1 equivalent per equivalent of bisphenol.

When one of these methods is employed, it is obvious that the crude bischloroformate product will ordinarily be obtained as a solution in a substantially non-polar organic liquid such as those disclosed hereinafter. Depending on the method of preparation, it may be desirable to wash said solution with a dilute aqueous acidic solution to remove traces of base used in preparation.

The tertiary amines useful as reagent B ("tertiary" in this context denoting the absence of N-H bonds) generally comprise those which are oleophilic (i.e., which are soluble in and highly active in organic media, especially those used in the method of this invention), and more particularly those which are useful for the formation of polycarbonates. Reference is made, for example, to the tertiary amines disclosed in the aforementioned U.S. Pat. No. 4,217,438 and in U.S. Pat. No. 4,368,315, the disclosure of which is also incorporated by reference herein. They include aliphatic amines such as triethylamine, tri-n-propylamine, diethyl-n-propylamine and tri-n-butylamine and highly nucleophilic heterocyclic amines such as 4-dimethylaminopyridine (which, for the purposes of this invention, contains only one active amine group). The preferred amines are those which dissolve preferentially in the organic phase of the reaction system; that is, for which the organic-aqueous partition coefficient is greater than 1. This is true because intimate contact between the amine and reagent A is essential for the formation of the cyclic oligomer mixture. For the most part, such amines contain at least about 6 and preferably about 6–14 carbon atoms.

The amines most useful as reagent B are trialkylamines containing no branching on the carbon atoms in the 1and 2- positions. Especially preferred are tri-n-alkylamines in which the alkyl groups contain up to about 4 carbon atoms. Triethylamine is most preferred by reason of its particular availability, low cost, and effectiveness in the preparation of products containing low percentages of linear oligomers and high polymers.

Reagent C is an aqueous alkali metal hydroxide solution. It is most often lithium, sodium or potassium hydroxide, with sodium hydroxide being preferred because of its availability and relatively low cost. The concentration of said solution is usually about 0.2–12 N.

The fourth essential component in the method of this invention (reagent D) is a substantially non-polar organic liquid which forms a two-phase system with water. The identity of the liquid is not critical, provided it possesses the stated properties. Illustrative liquids are aromatic hydrocarbons such as toluene and xylene; substituted aromatic hydrocarbons such as chlorobenzene, o-dichlorobenzene and nitrobenzene; chlorinated aliphatic hydrocarbons such as chloroform and methylene chloride; and mixtures of the foregoing with ethers such as tetrahydrofuran. Methylene chloride is preferred.

According to the present invention, the above-described reagents are simultaneously charged to a tank reactor. To avoid premature reaction, it is necessary to charge reagent A separately from reagents B and C. Most often, reagent A is combined with reagent D, the solvent, and the resulting solution is charged. Reagent B may also be charged as a solution in reagent D. Reagents B and C may be charged separately or in combination.

The conditions in the tank reactor are maintained so as to insure agitation (preferably by stirring) of the reaction mixture to a degree just sufficient to prevent segregation of the aqueous and organic liquid phases. Less effective agitation conditions decrease the yield of cyclic oligomer as a result of incomplete contact between the reagents, while agitation which is too rapid causes an increase in linears at the expense of cyclics. While the invention is not dependent on any theory of reaction, it is believed that formation of linear polycarbonates occurs interfacially, in similar manner to conventional polycarbonate production. Therefore, minimization of interfacial area is normally accompanied by an increase in the proportion of cyclics in the product.

It will be apparent to those skilled in the art that a number of parameters can affect the conditions of agitation. Among these are the design and location of charging means for the reagents; the design, location and speed of operation of agitating means; and the presence or absence and design of agitation facilitating means such as baffles in the reactor. It is generally preferred to introduce all reagents under the surface of the reaction mixture in the tank reactor. Other parameters can readily be adjusted by those skilled in the art with minimum experimentation so as to provide the required agitation conditions.

The reaction between the above-described reagents is allowed to proceed for a period of time sufficient to produce the desired cyclic polycarbonate oligomers. The residence time in the reaction vessel is usually in the range of about 6-30 minutes, especially about 8-16 and preferably about 8-12 minutes. It has been found that reaction is essentially complete irrespective of residence time. However, at shorter residence times the amount of linears in the product sharply increases, while at residence times greater than about 20 minutes, hydrolysis of the bischloroformate and/or cyclic oligomer product by the aqueous phase may occur, also leading to an increase in formation of linears.

Reaction temperature, considered in isolation, is not a crucial factor in the invention. There is seldom an advantage in operating below about 20° C., since the reaction rate may then be undesirably low. When the reaction is conducted at or near atmospheric pressure, temperatures above 100° C. are seldom warranted, in part because of the high energy input required. Under most circumstances, a temperature no higher than about 50° C. is appropriate. It is within the scope of the invention, but seldom advantageous, to operate above or below atmospheric pressure. However, higher temperatures may be employed if the method is conducted at elevated pressures.

In two respects, the temperature effect may be material. The first is the increasing disorder in the system as the temperature approaches reflux and then increases to increase the intensity of reflux. Such an increase in disorder should generally be accompanied by a decrease in externally provided agitation, so as to maintain the previously described conditions of agitation.

The second consideration is the effect of temperature on residence time. For example, the boiling point of methylene chloride is about 40° C. As that temperature is approached closely, there is a sharp increase in the volume of vapor in the system. Much vapor is present as bubbles in the liquid phase, decreasing the liquid volume in the reaction vessel.

The use of a continuous stirred tank reactor (hereinafter "CSTR") is advantageous under certain conditions to be described in more detail hereinafter. When a CSTR is employed, the residence time decreases in inverse proportion to the volume of vapor contained as bubbles in the liquid phase. This is one factor in the importance of reaction temperature, especially when a low boiling solvent such as methylene chloride is employed.

Balancing these factors, it is frequently found advantageous to operate at a reaction temperature from about 20° C. to at least 1° C. below the reflux temperature. When the solvent is methylene chloride, temperatures in the range of about 25°-39° C. are often convenient.

Another factor of some importance when a low boiling solvent is used is the avoidance of solvent loss by volatilization. Solvent loss, with a resulting decrease in the volume of the organic phase, can cause reproducibility problems if inefficient condensing means are utilized. It may be advisable under these circumstances to employ cooling temperatures as low as −70° to −75° C. in one or more condensers. It may also be advisable to provide a liquid seal on any CSTR outlet port, as described hereinafter.

The proportion of linears in the product is generally dependent to some extent on the proportion of reagent B, in terms of ratio of equivalents of B to A and concentration of B in moles per liter of reagent D. Under most circumstances, the ratio of equivalents of B to A should be in the range of about 0.05-1.0:1 and preferably about 0.15-0.4:1. (For the purposes of this invention, the equivalent weight of reagent A is half its average molecular weight and those of reagents B and C are equal to their molecular weights.) The concentration of reagent B is most often in the range of about 0.05-0.50 and preferably about 0.07-0.20 mole per liter of organic phase (i.e., all constituents except aqueous base) in the reaction mixture.

For the most part, other reaction conditions do not have as pronounced an effect on the composition of product as do the degree of agitation and residence time. However, it is generally found desirable to maintain a ratio of equivalents of reagent C to reagent A in the range of about 1.4-3.5:1 and preferably about 1.9-3.0:1. The volume ratio of aqueous to organic phase is ordinarily in the range of about 0.1-3.0:1.

After the desired residence time the desired cyclic oligomer product is recovered, typically by quenching of the reaction mixture by contact with an excess of water or, preferably, a dilute aqueous acid solution. The product is thus obtained as a solution in reagent D, from which it may be separated by conventional means such as evaporation of solvent or precipitation by addition of a non-solvent. At this stage it is also possible to separate from the cyclic oligomers any linears or other impurities. The degree of sophistication of recovery will depend on such variables as the intended end use of the cyclic oligomer composition.

The method of this invention is adaptable to both batch and continuous operation. Batch operation is often most conveniently effected by first charging the reaction vessel with a portion of reagent D and optionally also of reagents B and C, and subsequently adding reagent A and the remainder of reagents B, C and D.

A principal advantage of the invention is its adaptability to continuous operation. For this purpose, a CSTR may be employed. In addition to conventional reagent introduction means, agitation means and optional heating and/or cooling and agitation facilitating means, such a reactor has an outlet port for the continuous removal of product. The outlet port is typically located on the perimeter of the reactor, at a distance from the bottom sufficient to provide the desired liquid holdup and residence time in the reactor. To avoid loss of volatile solvents by vaporization, it is frequently preferred for the outlet port to have a suitable liquid seal, which may be provided by an inverted U-shaped bend or a similarly disposed right angle bend.

When a CSTR of the above-described design is used, there may be an interrelation between stirring rate and residence time. This is particularly true when the organic liquid employed is denser than water, as is true of methylene chloride and most other halogenated hydrocarbons. Under these conditions, if the stirring rate is too rapid a liquid-liquid centrifuge effect may cause premature discharge of a portion of the organic phase. It will be apparent that such premature discharge can be avoided by decreasing the stirring rate of the reaction mixture. This is another important reason why it is critical that the stirring rate not be excessive.

The invention is illustrated by the following examples.

EXAMPLE 1

The reaction vessel was a round-bottomed flask with a volume of 100 ml., fitted with an impeller stirrer, two reactant addition tubes immersed in the reaction mixture and pointed in a direction opposite to impeller rotation, and a condenser system comprising a tube condenser cooled to $-10°$ C. and a Dewar-type condenser cooled to $-72°$ C. An outlet port with a liquid seal was located in the wall of the vessel at a level to provide a liquid holdup of 50 ml.

Reagent A was a bisphenol A bischloroformate composition comprising about 27% monomer bischloroformate, about 43% dimer, trimer and tetramer bischloroformates and about 6% monomer monochloroformate, with the balance being higher bischloroformates; its molecular weight corresponded approximately to that of dimer bischloroformate. Reagent B was triethylamine, reagent C was 1.3 N aqueous sodium hydroxide solution and reagent D was methylene chloride.

The reaction vessel was initially charged with 31.4 ml. of methylene chloride, 18.6 ml. of sodium hydroxide solution and about 0.05 gram of triethylamine. There were then simultaneously introduced at 34°-35° C., with stirring, a 0.46 N bischloroformate solution in methylene chloride through one addition tube and a mixture of sodium hydroxide solution and a 1 N solution of triethylamine in methylene chloride simultaneously through the other addition tube. The reaction was run continuously at the following addition rates:
Bischloroformate solution—2.65 ml./min.
Triethylamine solution—0.45 ml./min.
Sodium hydroxide solution—1.83 ml./min.
These rates provided a residence time of 10.14 minutes in the reaction vessel, and the following other parameters:
Ratio of equivalents, B:A—0.37:1.
Ratio of equivalents, C:A—1.95:1.
Volume ratio, aqueous to organic phase—0.59:1.
Concentration of B—0.15 mole/liter organic phase.

The effluent from the reaction vessel was quenched by collection in a stirred vessel containing 3 N aqueous hydrochloric acid. At the end of the run, it was washed with 0.1 N HCl, the methylene chloride was removed by vacuum evaporation and the residue was analyzed by high pressure liquid chromatography to determine linears content.

The following percentages (by weight) of linears were obtained at various stirrer speeds (the balance being cyclics):
210 rpm.—16.8%.
400 rpm.—25.5%.
650 rpm.—36%.
1000 rpm.—50%.
These results show the importance of degree of agitation in obtaining products with a high proportion of cyclics and a low proportion of linears.

EXAMPLE 2

The reaction vessel was a flat-bottomed flask with straight vertical baffles and a volume of 100 ml., fitted with a two-tier impeller stirrer having four straight blades on each tier. An outlet port similar to that of Example 1 was placed to provide a liquid holdup of 80 ml. The addition tubes and condenser system were similar to those of Example 1.

Reagents A, B and D were the same as in Example 1. Reagent C was aqueous sodium hydroxide solution in the concentrations indicated below.

The reaction vessel was initially charged with 36 ml. of methylene chloride, 7.7 ml. of 1.005 N sodium hydroxide solution and 0.47 gram of triethylamine. The following were then added simultaneously, at the indicated rates, over 20 minutes at 35° C. with stirring at 275 rpm.:
Bischloroformate soln., 1.29 N in $CH_2Cl_2$ —1 ml./min.
Triethylamine (neat)—0.013 g./min.
Sodium hydroxide soln., 11.06 N—0.32 ml./min.

After the completion of the 20-minute addition period, continuous reagent addition was commenced. There were simultaneously added a 0.46 N bischloroformate solution in $CH_2Cl_2$, a 5.422 N sodium hydroxide solution and triethylamine (neat) at various rates, and product solution was continuously removed through the outlet port. In each instance, the triethylamine concentration was 0.13 mole per liter of organic phase and the volume ratio of aqueous to organic phase was 0.25:1. The product was recovered and analyzed as in Example 1.

The results are given in Table I.

TABLE I

| Residence time, min. | Addition rate, ml./min. | | | Linears, % |
|---|---|---|---|---|
| | Bischloroformate soln. | Triethylamine | NaOH soln. | |
| 5 | 12.6 | 0.23 | 3.2 | * |
| 8 | 7.9 | 0.14 | 2.0 | 15.6 |
| 12 | 5.2 | 0.094 | 1.33 | 16.0 |
| 16 | 3.9 | 0.071 | 1.00 | 17.5 |

*Product gelled due to high proportion of high molecular weight linears.

The figures in Table I show the advantage of operating in the preferred residence time range of 8–16 minutes and especially 8–12 minutes.

EXAMPLE 3

The reaction vessel and other equipment and reagents A, B and D were the same as in Example 1. Reagent C was aqueous sodium hydroxide solution in the concentrations indicated below.

The reaction vessel was initially charged with 36 ml. of methylene chloride, 12.32 ml. of 0.628 N aqueous sodium hydroxide solution and varying amounts of triethylamine. There were then added simultaneously, at the indicated rates, over 20 minutes at 35° C. with stirring at 275 rpm., various proportions of triethylamine (neat) and the following in the specified proportions:
Bischloroformate soln., 1.29 N in $CH_2Cl_2$—1 ml./min.
Sodium hydroxide soln., 6.911 N—0.504 ml./min.
These proportions provided the following parameters:
Ratio of equivalents, C:A—3.0:1.
Volume ratio, aqueous to organic phase—0.4:1.

After the 20-minute reaction period, the mixture was quenched, worked up and analyzed as described in Example 1.

The amounts of triethylamine in the various runs are listed in Table II, with proportion of linears listed for each run.

TABLE II

| Initial charge, mg. | Addition rate, mg./min. | Concentration, mols. per 1. $CH_2Cl_2$ | Equiv. ratio, B:A | Linears, % |
|---|---|---|---|---|
| 314.3 | 8.7 | 0.086 | 0.187 | 14.7 |
| 392.9 | 10.9 | 0.108 | 0.235 | 13.96 |
| 471.4 | 13.1 | 0.130 | 0.283 | 13.94 |
| 550.0 | 15.3 | 0.151 | 0.328 | 13.85 |
| 628.6 | 17.5 | 0.173 | 0.376 | 14.71 |

EXAMPLE 4

The procedure of Example 3 was repeated, varying the concentration and proportions of sodium hydroxide solution initially charged and added subsequently to afford various ratios of aqueous to organic phase. The results are listed in Table III.

TABLE III

| Sodium hydroxide | | | | | |
|---|---|---|---|---|---|
| Initial charge | | Subsequent addn. | | Volume ratio, aq./org. | Linear, % |
| Conc., N | Vol., ml. | Conc., N | Addition rate, ml./min. | | |
| 1.67 | 4.62 | 18.4 | 0.19 | 0.15 | 11.16 |
| 0.62 | 12.3 | 6.91 | 0.50 | 0.4 | 10.96 |
| 0.34 | 23.1 | 3.69 | 0.95 | 0.75 | 12.62 |

EXAMPLE 5

The procedure of Example 3 was repeated, varying the concentration of sodium hydroxide solution added after the initial charge to afford various ratios of equivalents of sodium hydroxide to bischoloroformate. The results are listed in Table IV.

TABLE IV

| NaOH conc., N | Equiv. ratio, C:A | Linears, % |
|---|---|---|
| 4.6 | 2.0 | 12.12 |
| 5.2 | 2.25 | 13.99 |
| 5.8 | 2.5 | 13.01 |
| 6.9 | 3.0 | 13.83 |
| 8.1 | 3.5 | 19.1 |

What is claimed is:

1. A method for preparing a composition comprising cyclic polycarbonate oligomers characterized by structural units of the formula

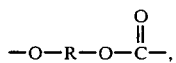

where R is a divalent aromatic radical, which comprises:
simultaneously charging the following to a tank reactor:
(A) a bischloroformate composition consisting essentially of bischloroformates of the formula

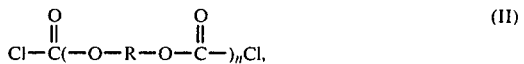

wherein n is at most 3 in a major proportion of said bischloroformates;
(B) at least one aliphatic or heterocyclic tertiary amine which dissolves preferentially in the organic phase of the reaction mixture;
(C) an aqueous alkali metal hydroxide solution; and
(D) a substantially non-polar organic liquid which forms a two-phase system with water;
reagent A being charged separately from reagents B and C:
while maintaining the reaction mixture in said tank reactor under agitation conditions just sufficient to prevent segregation of the aqueous and organic liquid phases;
allowing said reagents to react for a period of time sufficient to form the desired cyclic oligomers; and recovering said oligomers.

2. A method according to claim 1 wherein R has the formula

wherein each of $A^1$ and $A^2$ is a single-ring divalent aromatic radical and Y is a bridging radical in which one or two atoms separate $A^1$ from $A^2$.

3. A method according to claim 2 wherein the reaction temperature is in the range of about 20°–50° C.

4. A method according to claim 3 wherein reagents A, B, C and D are introduced under the surface of the reaction mixture in the tank reactor.

5. A method according to claim 4 wherein the reactor is a continuous stirred tank reactor and the reaction is conducted continuously.

6. A method according to claim 5 wherein reagent B is triethylamine.

7. A method according to claim 6 wherein reagent C is a sodium hydroxide solution.

8. A method according to claim 7 wherein reagent D is methylene chloride.

9. A method according to claim 8 wherein the reaction temperature is in the range of about 25°–39° C.

10. A method according to claim 9 wherein each of $A^1$ and $A^2$ is p-phenylene and Y is isopropylidene.

11. A method according to claim 10 wherein reagent A is a crude bischloroformate product comprising a major proportion of bischloroformates containing up to 4 structural units.

12. A method according to claim 11 wherein the residence time of the reaction mixture is in the range of about 8–16 minutes.

13. A method according to claim 12 wherein the ratio of equivalents of B to A is in the range of about 0.15–4.0:1.

14. A method according to claim 13 wherein the concentration of reagent B is in the range of about 0.07–0.20 mole per liter of total reagent D in the reaction mixture.

15. A method according to claim 14 wherein the ratio of equivalents of C to A is in the range of about 1.9–3.0:1.

16. A method according to claim 15 wherein the volume ratio of aqueous to organic phase is in the range of about 0.1–3.0:1.

* * * * *